(12) United States Patent
Harrell

(10) Patent No.: US 9,884,078 B2
(45) Date of Patent: *Feb. 6, 2018

(54) HUMAN AMNIOTIC FLUID PREPARATION HAVING LONG-TERM STABILITY

(71) Applicant: MAM Holdings of West Florida, L.L.C., Tarpon Springs, FL (US)

(72) Inventor: Carl Randall Harrell, Tarpon Springs, FL (US)

(73) Assignee: MAM HOLDINGS OF WEST FLORIDA, L.L.C., Tarpon Springs, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/435,878

(22) Filed: Feb. 17, 2017

(65) Prior Publication Data

US 2017/0246216 A1 Aug. 31, 2017

Related U.S. Application Data

(63) Continuation of application No. 15/053,497, filed on Feb. 25, 2016, now Pat. No. 9,579,350.

(51) Int. Cl.
*A61K 35/50* (2015.01)
*A61K 38/17* (2006.01)
(Continued)

(52) U.S. Cl.
CPC .............. *A61K 35/50* (2013.01); *A61K 38/17* (2013.01); *A61K 38/1774* (2013.01); *A61K 38/18* (2013.01); *A61K 38/185* (2013.01); *A61K 38/1808* (2013.01); *A61K 38/1825* (2013.01); *A61K 38/1841* (2013.01); *A61K 38/1858* (2013.01); *A61K 38/1866* (2013.01); *A61K 38/191* (2013.01); *A61K 38/193* (2013.01); *A61K 38/195* (2013.01); *A61K 38/20* (2013.01); *A61K 38/204* (2013.01); *A61K 38/2006* (2013.01); *A61K 38/208* (2013.01); *A61K 38/2033* (2013.01); *A61K 38/2053* (2013.01);
(Continued)

(58) Field of Classification Search
CPC ...................................................... A61K 35/50
See application file for complete search history.

(56) References Cited

U.S. PATENT DOCUMENTS 9,132,156 B1 * 9/2015 Werber .................. A61K 35/50

OTHER PUBLICATIONS

Adzick, et al., "Cells, matrix, growth factors, and the surgeon. The biology of scarless fetal wound repair", Ann Surg, 220:10 8 (1994).
(Continued)

*Primary Examiner* — Benjamin Packard
(74) *Attorney, Agent, or Firm* — Pabst Patent Group LLP

(57) ABSTRACT

Methods of preparing sterile de-cellularized human amniotic fluid that is amenable for long-term storage without loss of biological functions have been developed. In particular, the methods involve refrigeration steps to maximize shelf-life while retaining most of the important growth factors and other molecules present in the fresh amniotic fluid for effective therapeutic application. Use of the compositions is intended for therapeutic purposes and will alleviate pain or discomfort associated with any disorders or diseases, particularly those involving eyes and joints, or fibrotic disorders such as COPD.

18 Claims, 6 Drawing Sheets

(51) Int. Cl.
*A61K 38/18* (2006.01)
*A61K 38/19* (2006.01)
*A61K 38/20* (2006.01)
*A61K 38/21* (2006.01)
*A61K 38/48* (2006.01)

(52) U.S. Cl.
CPC ...... *A61K 38/2066* (2013.01); *A61K 38/2086* (2013.01); *A61K 38/217* (2013.01); *A61K 38/4886* (2013.01); *A61L 2400/06* (2013.01); *A61L 2430/24* (2013.01)

(56) References Cited

OTHER PUBLICATIONS

Anker, et al., "Amniotic fluid as a novel source of mesenchymal stem cells for therapeutic transplantation", Blood, 102:1548 9 (2003).
Duffy, et al., "Vascular Endothelial Growth Factor (VEGF) and Its Role in Non-Endothelial Cells: Autocrine Signalling by VEGF", In: Madame Curie Bioscience Database [Internet]. Austin (TX): Landes Bioscience (2000).
Gao, et al., "Effects of amniotic fluid on proteases: a possible role of amniotic fluid in fetal wound healin", Ann Plastic Surg, 33:128 34 (1994).
Hoeben, et al., "Vascular endothelial growth factor and angiogenesis", Pharmacol Rev, 56:549-80 (2004).
Maraldi, et al., "Role of hepatocyte growth factor in the immunomodulation potential of amniotic fluid stem cells", Stem Cells Transl Med, 4(6):539-47 (2015).
Nagase, et al., "Structure and function of matrix metalloproteinases and TIMPs", Cardiovasc Res., 69(3): 562-73 (2006).
Ozgenel, et al., "Effects of human amniotic fluid on peripheral nerve scarring and regeneration in rats", J Neurosurg, 98:371 7 (2003).
Sporn, et al., "Transforming growth factor-beta: biological function and chemical structure", Science, 233(4763) 532-4 (1986).
Todderud, et al., "Epidermal growth factor: the receptor and its function", Biofactors., 2(1):11-5 (1989).
Yun, et al., "Fibroblast growth factors: biology, function, and application for tissue regeneration", J Tissue Eng, 218142. doi:1-18 (2010).

* cited by examiner

HUMAN AMNIOTIC FLUID PREPARATION HAVING LONG-TERM STABILITY

CROSS REFERENCE TO RELATED APPLICATIONS

This application is a continuation of U.S. Ser. No. 15/053,497, filed Feb. 25, 2016, the disclosure of which is hereby incorporated herein by reference in their entirety.

FIELD OF THE INVENTION

The invention is generally directed to methods of preparing sterile de-cellularized human amniotic fluid that is stable during long-term storage with minimal to no loss of biological functions of molecules naturally present in the raw amniotic fluid, dosage units and new uses thereof.

BACKGROUND OF THE INVENTION

Amniotic fluid (AF) is a complex and dynamic milieu that changes as pregnancy progresses. AF contains nutrients and growth factors that facilitate fetal growth, provides mechanical cushioning and antimicrobial effectors that protect the fetus, and allows assessment of fetal maturity and disease.

AF contains a plethora of factors including carbohydrates, proteins and peptides, lipids, lactate, pyruvate, electrolytes, enzymes, and hormones. AF contains many important growth factors including epidermal growth factor (EGF), transforming growth factor alpha (TGF-α), transforming growth factor beta-1, insulin-like growth factor I (IGF-I), and erythropoietin (EPO).

Human AF contains factors that appear to minimize scarring (Ozgenel G Y et al., *J Neurosurg* 2003; 98: 371-377). Amniotic factors that potentially contribute to the wound healing process include hyaluronic acid, which is found in high levels in AF, inhibits collagen synthesis. This hyaluronic acid-rich environment is due to a relative lack of hyaluronidase in AF and to the presence of hyaluronic acid-stimulating factor in AF. In one study looking at the effect of AF on proteases important to wound healing, human AF was shown to enhance collagenase activity, but to inhibit activities of hyaluronidase, elastase, and cathepsin (Gao X et al., *Ann Plastic Surg* 1994; 33: 128-134). In addition, TGF-β may also play a major role in scar formation (Adzick NsS et al., *Ann Surg* 1994; 220: 10-18).

Furthermore, human AF has been evaluated as a source for stem cells (In't Anker P S et al., *Blood* 2003; 102: 1548-1549).

It is unclear whether important amniotic factors can survive processes such as centrifugation, filtration, refrigeration, freezing, and long-term storage.

Therefore, it is an objective of the current invention to provide methods for enhancing the stability of amniotic fluids for long-term storage at temperatures above freezing.

It is also an objective of the current invention to provide methods for purification of amniotic fluid that maximize the stability of critical amniotic factors present in the raw amniotic fluid for therapeutic applications.

It is a further objective of this current invention to provide dosage units and formulations that are readily accessible and easy to use for both the clinician and patient, as well as new uses thereof.

SUMMARY OF THE INVENTION

Methods for preparation of de-cellularized human amniotic fluid (D-HAF) amenable to storage for extended periods of time are provided. Generally, the methods include collecting amniotic fluid from pregnant women just prior to cesarean procedure, followed by de-cellularizing the amniotic fluid via centrifugation and a series of filtration steps prior to storage in sterile vessels. D-HAF is stored in bulk or in small aliquots such as in individual syringes or vials ready for application. D-HAF is stored as a liquid under refrigerated conditions at about 1° C. to about 10° C. or under freezing conditions at about −20° C. to about −85° C. Alternatively, D-HAF is lyophilized to be stored as a dry powder at about −85° C. to about 25° C.

The amniotic fluid preparation can be formulated into pharmaceutical compositions. Generally, D-HAF compositions retain most amniotic factors after short-term or long-term storage under temperature-controlled conditions either as a liquid or as lyophilized powder. D-HAF after storage retains at least 50% of the total protein content compared to that of the fresh D-HAF, preferably more than 80%. In a preferred embodiment, refrigeration of the D-HAF is used to reduce levels of one or more inflammatory molecules such as Eotaxin-2, IL-6, PARC/CCL18, total GRO, ENA-78/CXCL-5, 6Ckine, and MIP-3α.

The D-HAF has a variety of uses based on the concentrations of growth factors and low toxicity and inflammation. In one embodiment, the formulation is injected into areas with wrinkles, thin skin, or poor healing. In another embodiment, the formulation is administered directly to the eye to treat dry eye due to aging or long term contact use. In another embodiment, the formulation is administered as an aerosol to alleviate one or more symptoms of chronic obstructive pulmonary disease ("COPD"). In another preferred embodiment, the D-HAF is administered into a joint to alleviate pain or enhance healing.

The D-HAF is packaged into sterile dosage units which can be stored and distributed for use by attending physicians. These lyophilized or fluid formulations can be in the form of sterile packaged syringes for injection, dropper bottles (typically a 30 day supply for application once or twice daily to the eye), aerosols, or tubes or jars of creams or lotions. The dosages for the Injectables will be 0.25 cc/0.5 cc and 1.0 cc. The injectables can be administered subcutaneously ("sc"), intramuscularly ("im"), or into a joint. The efficacy is determined by Physician evaluations, patient self evaluations, imaging studies and Quality of life evaluations.

BRIEF DESCRIPTION OF THE DRAWINGS

FIG. 3A shows notable amniotic factors decreased in the raw fluid including VEGF-α, TNF-α and HGF. FIG. 3B shows notable amniotic factors decreased in the D-HAF sample stored at 2-8° C. including FGF7, MMP-9, GCSF, MMP-7, MMP-13, TGF-β, FGF-4, EG-VEGF and IL-8. FIG. 3C shows notable amniotic factors decreased in the D-HAF sample stored at −85° C. including FGF-21, ANG2, GDNF, FGF-19, TIMP-2, ANG-1, TGFβ1 and M-CSF FIG. 3D shows variable changes in amniotic factors including Angiotensinogen, PDGF-AA, TGF-α, EGF and SCF.

FIG. 4A shows notable inflammatory factors decreased in the raw fluid including MIP-1β, TGFα and MCP-2. Some inflammatory factors that were not detected (ND) in the samples include IFN-γ, IL-1β and IL-12p40. FIG. 4B shows notable inflammatory factors decreased in the D-HAF sample stored at 2-8° C. including Eotaxin-2, IL-6, PARC/CCL18, total GRO, ENA-78/CXCL-5, 6Ckine and MIP-3α. FIG. 4C shows notable inflammatory factors decreased in the D-HAF sample stored at −85° C. including MIG/CXCL-9, MIP-1α, RANTES/CCL-5 and IL-1α.

FIG. 5A shows notable anti-inflammatory factors decreased in the raw fluid including IL-5, VEHF-A, IL-21 and VEGF-D. FIG. 5B shows notable anti-inflammatory factors decreased in the D-HAF sample stored at 2-8° C. including IL-8, IL-13, IL-27 and CTLA-4. FIG. 5C shows notable anti-inflammatory factors decreased in the D-HAF sample stored at −85° C. including IL-1Ra and TGFβ1.

DETAILED DESCRIPTION OF THE INVENTION

I. Definitions

Figure 1:
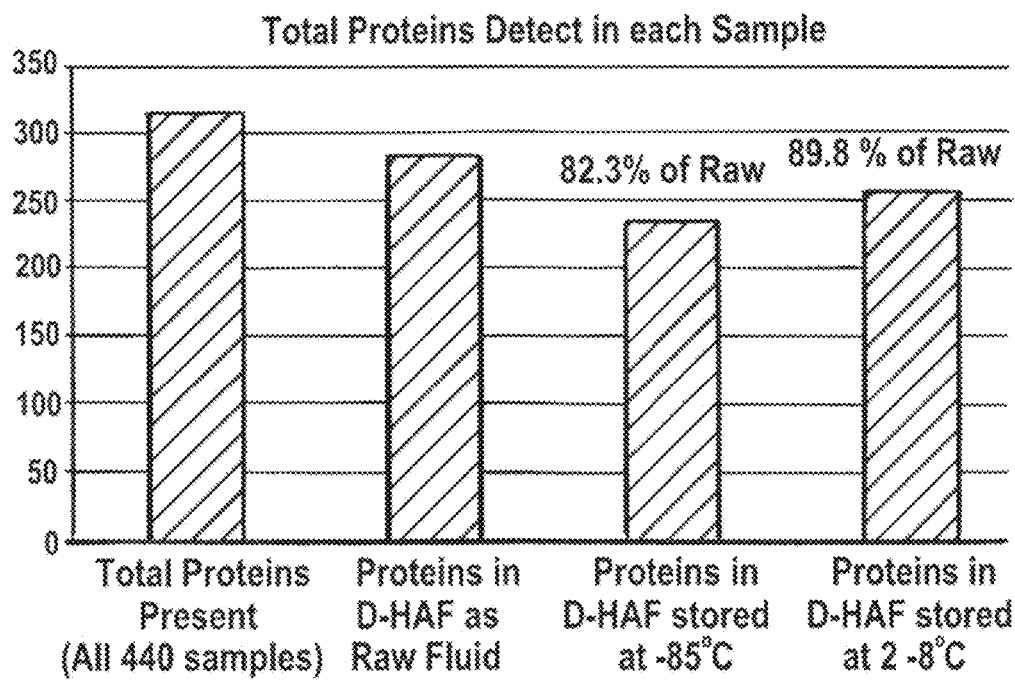
FIG. 1 is a bar graph showing total protein content for samples containing raw fluid; and sterile de-cellularized human amniotic fluid (D-HAF) stored at −85° C.; and sterile D-HAF stored at 2-8° C., respectively.

The term "Active Agent," refers to a physiologically or pharmacologically active substance that acts locally and/or systemically in the body. An active agent is a substance that is administered to an individual for the treatment (e.g., therapeutic agent), prevention (e.g., prophylactic agent), or diagnosis (e.g., diagnostic agent) of a disease or disorder. For example, the term "Ophthalmic Active Agent", or "Ophthalmic Drug", as used herein, refers to an agent that is administered to a patient to alleviate, delay onset of, or prevent one or more symptoms of a disease or disorder of the eye or a component thereof. Active agents may also include materials that alleviate wrinkles, restore bulk or muscle or tissue tone, or other cosmetic used.

The term "effective amount" or "therapeutically effective amount," refers to an amount effective to alleviate, delay onset of, or prevent one or more symptoms of a disease or disorder.

The term "growth factors," refers to a group of proteins or hormones that stimulate the cellular growth. Growth factors play an important role in promoting cellular differentiation and cell division, and they occur in a wide range of organisms.

The term "amniotic factor," generally refers to molecules naturally present in the amniotic fluid. These include carbohydrates, proteins and peptides such as enzymes and hormones, lipids, metabolic substrates and products such as lactate and pyruvate, and electrolytes.

The term "biocompatible" or "biologically compatible," generally refers to materials that are, along with any metabolites or degradation products thereof, generally non-toxic to the recipient, and do not cause any significant adverse effects to the recipient. Generally speaking, biocompatible materials are materials which do not elicit a significant inflammatory or immune response when administered to a patient.

The term "pharmaceutically acceptable," refers to compounds, carriers, excipients, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "molecular weight," generally refers to the relative average chain length of the bulk polymer, unless otherwise specified. In practice, molecular weight can be estimated or characterized using various methods including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

II. Compositions

A. Amniotic Growth Factors, Cytokines and Other Molecules

Amniotic fluid ("AF") contains nutrients and growth factors that facilitate fetal growth, provides mechanical cushioning and antimicrobial effectors that protect the fetus, and allows assessment of fetal maturity and disease. AF typically contains mixtures of growth factors, pro-inflammatory cytokines and anti-inflammatory cytokines, as well as a variety of macromolecules including carbohydrates, proteins and peptides, lipids, lactate, pyruvate, electrolytes, enzymes, and hormones.

Growth factors and their receptors control a wide range of biological functions, regulating cellular proliferation, survival, migration and differentiation. Growth factors found in AF play a critical role in fetal growth and development.

A non-limiting list of growth factors that have been identified in AF includes such as epidermal growth factor (EGF), insulin-like growth factor I (IGF-I), vascular endothelial growth factor A (VEGF-α), tumor necrosis factor A (TNF-α), hepatocyte growth factor (HGF), fibroblast growth factor 7 (FGF7), matrix metallopeptidase (MMP-9), granulocyte-colony stimulating factor (GCSF), matrix metalloproteinase-7 (MMP-7), matrix metalloproteinase-7 (MMP-13), transforming growth factor alpha (TGF-α), transforming growth factor beta (TGF-β), fibroblast growth factor 4 (FGF-4), endocrine gland-derived vascular endothelial growth factor (EG-VEGF), interleukin 8 (IL-8), fibroblast growth factor 21 (FGF-21), angiopoietin-2 (ANG2), Glial cell-derived neurotrophic factor (GDNF), fibroblast growth factor 19 (FGF-19), TIMP metallopeptidase inhibitor 2 (TIMP-2), angiopoietin-1 (ANG-1), Transforming growth factor beta 1 (TGFβ1), macrophage colony-stimulating factor (M-CSF), angiotensinogen, platelet derived growth factor-AA (PDGF-AA), and stem cell factor (SCF).

Epidermal growth factor (EGF) is a small polypeptide hormone with mitogenic properties in vivo and in vitro. EGF elicits biologic responses by binding to a cell surface receptor which is a transmembrane glycoprotein containing a cytoplasmic protein tyrosine kinase. EGF responses are mediated by ligand binding and activation of this intrinsic protein kinase. The receptor can be phosphorylated by other protein kinases, and this may regulate receptor function. Stimulation of the receptor tyrosine kinase activity by ligand binding must regulate the activity of an as yet undefined molecule(s) responsible for transmitting a mitogenic signal to the nucleus (Todderud G, et al., Biofactors. 1989, 2(1): 11-5).

Vascular endothelial growth factor (VEGF), also known as vascular permeability factor (VPF), was originally described as an endothelial cell-specific mitogen. VEGF is produced by many cell types including tumor cells, macrophages, platelets, keratinocytes, and renal mesangial cells. The activities of VEGF are not limited to the vascular system; VEGF plays a role in normal physiological functions such as bone formation, hematopoiesis, wound healing, and development (Duffy A M et al., In: Madame Curie Bioscience Database [Internet]. Austin (Tex.): Landes Bioscience (2000)).

TGF-α has a structure similar to EGF and binds to the same receptor. The amnion cells of the umbilical cord express EGF, TGF-α, and the functional EGF/TGF-α receptor, suggesting the possibility of a regulating role of the amnion in fetal growth and development. EGF and TGF-α have also been shown to stimulate the production of surfactant components. TGFβ1 is believed to induce terminal differentiation of intestinal epithelial cells and to accelerate the rate of healing of intestinal wounds by stimulating cell migration. TGFβ1 may also stimulate IgA production. VEGF-A is a signal protein that stimulates vasculogenesis and angiogenesis (Hoeben Am, et al., *Pharmacol Rev* 2004, 56:549-580).

Transforming growth factor-beta (TGF-β) is a multifunctional peptide that controls proliferation, differentiation, and other functions in many cell types. Many cells synthesize TGF-beta and essentially all of them have specific receptors for this peptide. TGF-beta regulates the actions of many other peptide growth factors and determines a positive or negative direction of their effects (Sporn M B, et al., Science 1986, 233(4763) 532-534).

Hepatocyte growth factor (HGF), the ligand for the receptor tyrosine kinase encoded by the c-Met proto-oncogene, is a multidomain protein structurally related to the pro-enzyme plasminogen and with major roles in development, tissue regeneration and cancer. A recent study showed its immunomodulation potential of amniotic fluid stem cells (Maraldi T, et al. *Stem Cells Transl Med*, 4(6):539-47 (2015)).

Fibroblast growth factors (FGFs) that signal through FGF receptors (FGFRs) regulate a broad spectrum of biological functions, including cellular proliferation, survival, migration, and differentiation. The FGF signal pathways are the RAS/MAP kinase pathway, PI3 kinase/AKT pathway, and PLCγ pathway, among which the RAS/MAP kinase pathway is known to be predominant. Several studies have recently implicated the in vitro biological functions of FGFs for tissue regeneration. Many current applications of FGF are in regeneration of tissues, including skin, blood vessel, muscle, adipose, tendon/ligament, cartilage, bone, tooth, and nerve tissues (Yun Y R, et al., J Tissue Eng 2010: 1(1)).

Matrix metalloproteinases (MMPs), also called matrixins, function in the extracellular environment of cells and degrade both matrix and non-matrix proteins. They play central roles in morphogenesis, wound healing, tissue repair and remodelling in response to injury, e.g. after myocardial infarction, and in progression of diseases such as atheroma, arthritis, cancer and chronic tissue ulcers. They are multidomain proteins and their activities are regulated by tissue inhibitors of metalloproteinases (TIMPs) (Nagase H, et al., Cardiovascular Research, European Society of Cardiology, 562-573).

Amniotic fluid also contains many pro- and anti-inflammatory cytokines. Pro- and anti-inflammatory cytokines play important immunoregulatory roles. Inflammation is characterized by interplay between pro- and anti-inflammatory cytokines. Cytokines are commonly classified in one or the other category: interleukin-1 (IL-1), tumor necrosis factor (TNF), gamma-interferon (IFN-gamma), IL-12, IL-18 and granulocyte-macrophage colony stimulating factor are well characterized as pro-inflammatory cytokines whereas IL4, IL-10, IL-13, IFN-alpha and transforming growth factor-beta are recognized as anti-inflammatory cytokines.

Exemplary pro-inflammatory cytokines include Eotaxin-2 (CCL24), interleukin 6 (IL-6), pulmonary and activation-regulated chemokine PARC or chemokine (C-C motif) ligand 18 (CCL18), total GRO which consisted of three subunits GROα/CXCL1, GROβ/CXCL2, and GROγ/CXCL3, expression of the neutrophil-activating CXC chemokine (ENA-78/CXCL-5), chemokine (C-C motif) ligand 21 (CCL21 or 6Ckine), macrophage inflammatory protein 3 alpha (MIP-3α or CCL20), monokine induced by gamma (MIG or CXCL-9), MIP-1α, chemokine (C-C motif) ligand 5 (CCL-5), also known as RANTES (regulated on activation, normal T cell expressed and secreted), Interleukin-1 alpha (IL-1α), macrophage inflammatory protein-1β (MIP-1β or CCL4), tumor necrosis factor (TGFα) and monocyte chemotactic protein 2 (MCP-2 or CCL8).

Exemplary anti-inflammatory cytokines include the anti-inflammatory factors include interleukin 8 (IL-8), interleukin 13 (IL-13), interleukin 27 (IL-27), cytotoxic T-lymphocyte-associated protein 4 (CTLA-4), vascular endothelial growth factor D (VEGF-D), interleukin-1 receptor antagonist (IL-1Ra), transforming growth factor beta 1 (TGFβ1), interleukin 5 (IL-5) and interleukin 21 (IL-21).

B. Dilute Amniotic Fluid Formulation

Formulations of purified amniotic fluid are provided. Typically, the formulations include diluted sterile de-cellularized human amniotic fluid (D-HAF), either in fluid form or lyophilized, alone or in combination with appropriate excipients. Other active agents may be included. D-HAF contains over 300 human growth factors. D-HAF is devoid of amniotic stem cells and elements of micronized membrane or chorion particles. The purified fluid is sterilized without the use of harsh terminal irradiation, e-beam or Ethylene Oxide (EO). In the preferred embodiment, the process consists of separating the cells from the AF using centrifugation and utilizing a series of filtration devices to remove all remaining cells and bioburden. Each lot is tested for bioburden and is certified sterile to contain <1 harmful organisms.

Method of Preparation

The formulation is prepared from sterile human amniotic fluid obtained from a pregnant woman. The formulation is free of amniotic membrane particulate matter, i.e. cells, large particles and other undissolvables are removed, preferably by high speed centrifugation to obtain clarified amniotic fluid. The clarified amniotic fluid is then filtered through filters having a pore size of about 5μ to about 10μ to obtain a micron filtrate, followed by filtering the micron filtrate through filters with a pore size of about 1.0μ to obtain a second filtrate, followed by filtering the filtrate through submicron filters with the pore size of 0.45μ or/and 0.2μ to obtain the sterilely filtered amniotic fluid.

Those of skill in the art are well-acquainted with methods of safely and humanely obtaining samples of AF, and of the need to maintain sterility of the AF during such procedures. Suitable sources, e.g. of human AF, include AF that is obtained from patients who are undergoing amniocentesis, patients who are undergoing a Caesarean section delivery, and patients undergoing normal delivery using a specially designed receptacle to collect the fluid after rupture of membranes.

In one embodiment, the collection procedure is performed in a sterile operating room environment during an elective C-section. Typically, the woman is undergoing a pre-caesarian surgical method, and the step of obtaining the sterile human amniotic fluid includes the steps of turning on a ultrasound device to provide guidance for the process of obtaining human fluid from the woman, inserting a blunt tip needle into the amniotic sac of the woman, attaching the blunt tip needle to a three-way stopcock, connecting a Luer lock syringe to the three-way stopcock, connecting a first end of a length of sterile tubing with the three-way stopcock, and collecting sterilely the amniotic fluid through the blunt tip needle and sterile tubing into a collection container.

In this embodiment, the sterile collection container includes a pump with a suction device. The suction device is a low suction device or a spring loaded low suction device. The suction device is fluidly connected to an internal balloon. This embodiment further includes manually pumping up the internal balloon in the sterile collection container using the low suction device to allow a low-level suction and collection of the amniotic fluid.

In one embodiment, the AF collected is stored and shipped at 2-8° C. Shipments are made overnight in insulated cooler boxes with ice packs.

All processing is done under sterile conditions, in a Class 100 laminar flow hood in a clean room. As much AF as possible is separated from any solid debris. AF is transferred to sterile 500-2,000 mL containers (size depends on initial volume). Processing is performed at below 25° C. during the process.

The step of removing cells, large particles and other solids from the human amniotic fluid includes a first step of centrifuging or depth filtering the human amniotic fluid. In some embodiments, the human amniotic fluid is centrifuged at about 5,000 rpm to about 10,000 rpm for about 30 minutes to about 60 minutes. Peristaltic pumps are used to transfer the AF to clean, sterile 250 mL centrifuge bottles without over-filling the bottles. The weight of each bottle should not vary more than 2.0 grams when placed in the rotor. Use the sterile rotor sleeves over the bottles to keep them clean. Spin the bottles at 10,000 rpm for 60 minutes in the Sorvall refrigerated centrifuge. Delicately decant or pump the supernatant to a sterile container and save the pellet material. An optional second centrifugation is used when the AF is not clear of debris after the initial centrifugation. In one embodiment, the AF supernatant from the first centrifugation is transferred to sterile 50 mL centrifuge tubes which are spun at 5,000 rpm for 60 minutes. AF supernatant is decanted into a sterile container and any significant pellet volume saved.

The AF supernatant is subsequently subject to a series of filtration steps. In one embodiment about 5μ to about 10μ filters are used for the first filtration (pre-filtration) are cellulose ester filters, glass fiber filters, nylon capsule filters or nylon cartridge filters. In some embodiments, multiple pre-filters are used, depending on the clarity of the filtered solution. The filters with the pore size of 1.0μ (Filtration 1.0u) are capsule filters or cartridge filters. The filters with the pore size of 1.0μ are poly ether sulfone, poly vinylidene fluoride or cellulose acetate membrane filters. Final filtration is carried out using filters with the pore size of 0.45μ or 0.2μ which are capsule filters or cartridge filters. The filters with the pore size of 0.45μ or 0.2μ are poly ether sulfone membrane filters, poly vinylidene fluoride or cellulose acetate membrane filters.

The sterilely filtered human amniotic fluid contains growth factors including human growth hormone, transforming growth factor beta 1, vascular endothelial growth factor, epidermal growth factor, transforming growth factor beta 3, and growth differentiation factor 11 or combinations thereof.

The sterile amniotic fluid further includes the step of filling and packaging. For example, sterile D-HAF is filled in syringes ready for application. Each shot should weigh 0.90-1.10 grams. Recalibrate pump settings if needed. Begin the fill operation using the nests of 100 Schott TopPaclmL syringes. Purge the air 3× from the Impro stoppering system. Stopper each nest immediately after filling using the Impro vacuum stoppering system connected to 0.2μ filtered air. Aseptically perform at least (3) particulate counts and open media controls over the course of the run.

In a further embodiment, the filled syringes are capped with a sterile plunger. Place the syringe in a Mangar mylar pre-labeled pouch with the plunger rod towards the chevron side of the pouch. Seal the pouch with a heat sealer set to 270° F., 2.4 second dwell, 170° F. cooling temperature. Visually inspect the seals after sealing. Note that the intact syringe constitutes the primary sterile barrier of the AF product.

In yet another embodiment, the AF fluid is filled in sterile 2 cc vials with stoppers and 13 mm crimp caps as a barrier.

In some embodiments, the sterile amniotic fluid further includes the step of lyophilizing the sterile amniotic fluid to obtain a lyophilisate thereof. The method further includes irradiating the lyophilisate by e-beam irradiation or gamma ray irradiation to reinforce the sterility.

In some embodiments, the amniotic fluid from the final filtration is aseptically transferred to syringes or vials, and kept in a deep freezer at about −80° C. to about −20° C. for long term storage. The sterile amniotic fluid is dried in the vial via lyophilization in a built-in a sterile environment. The lyophilisate derived from the amniotic fluid is reconstituted with sterile water before injection or topical administration. The lyophilisate can be stored at from +4° C. to about +25° C. (room temperature).

If needed, the lyophilisate derived from amniotic fluid through lyophilization may be irradiated by e-beam irradiation or gamma ray irradiation to add another guarantee for the final sterility of the powder. Irradiation of a lyophilisate is much less denaturing for proteins and peptides than irradiating aqueous solutions, because the absence of water considerably reduces the production of reactive superoxide anions and their diffusion during irradiation. Such superoxide anions are the main cause of splitting peptide bonds and chemically modifying amino acids of protein and peptides. After lyophilization, the amniotic fluid is reconstituted by adding the initial volume of water. After gentle homogenization, the powder is quickly dissolved in about one minute.

The reconstituted amniotic liquid is transparent and may be used for wound healing, cosmetic, orthopedic, or ophthalmic applications, particularly for the treatment of dry eyes.

Tools to obtain sterilely filtered human amniotic fluid from a woman, include a three-way stopcock, a sterile blunt tip needle aseptically attached to the three-way stopcock, a Luer lock syringe aseptically connected to the three-way stopcock, a sterile tubing aseptically connected to the three-way stopcock, a collection container or a collection container including a pump with suction device connected with the sterile tubing, a set of filters having the pore size of about 5μ to about 10μ, a set of capsule or cartridge filters having the pore size of about 1μ, a set of capsule or cartridge filters having the pore size of about 0.45μ or 0.2μ, a set of sterile syringes or vials to store the sterile filtered amniotic fluid and operating instructions on using the kit to obtain sterilely filtered human amniotic fluid. The filters having the pore size of from about 5μ to about 10μ and the capsule or cartridge filters are made from cellulose ester, glass fiber or nylon.

The sterile collection container may include a pump with a suction device. In one aspect of this embodiment suction device may be a low suction device or spring loaded low suction device. In another aspect the suction device may be fluidly connected to an internal balloon. Further to this aspect the method includes manually pumping up the internal balloon in the sterile collection container using the low suction device to allow a low-level suction and collection of the amniotic fluid. In yet another aspect the sterile collection container may include an inlet. Further to this particular aspect the method includes connecting a second end of the tubing to the inlet of the sterile collection container. The sterile collection container may include a vent having a cap.

Utilizing the incision site immediately prior to performing the C-section and with ultrasound guidance to protect the fetus and mother provides a minimal or no risk environment for collection. Collection is achieved via a low level suction established within a collection container and/or via gravity.

Typically, high speed centrifugation filtration with 5 to 10μ filters (low protein binding filter) is used to complete the removal of cells and large particles. Submicron filtration would then be conducted with 1μ and 0.45μ or/and 0.2μ filters (low protein binding filter), two in a series connection, to remove gross contaminates. Under this condition, soluble growth factors will pass through this filter to achieve a semi-sterile condition, very low bioburden counts. If under a strict aseptic operation condition, a $10^{-3}$ sterility assurance level is achieved. A $10^{-6}$ sterility assurance level can be achieved by submicron filtration with a 0.22μ filter (low protein binding filter) at the end and sterile packaging to achieve a sterile product. One would monitor the filtrate after each filtration step to determine which components were removed and then to determine which process to use to achieve the desirable product.

One may use membrane filters including or made of hydrophilic polyethersulphone (PES) to filter protein solutions. Filter disks for small volumes and different sizes of cartridges for larger volumes such 1 liter and more. Hydrophobic membranes like PTFE which are designed for liquids devoid of proteins should not be used. Start with centrifugation at 5000 to 8000 rpm for at least 30 minutes. Next, the supernatant is filtered with a prefilter to remove residual protein aggregates and precipitates in suspension (AP20 can be used). If one directly uses a 0.6/0.2 μm filter, after prefiltration, one may experience slow filtration rates and the flow may stop too quickly. It may be desirable to make intermediate filtration steps using 1.2μ and 0.8μ membranes. Typically, a final filtration through 0.2μ is necessary to get the best sterility assurance level and produce a sterile amniotic fluid for injections.

Methods of Storage

The final filtrate can be stored in frozen condition at about −20° C. to about −80° C. for long-term storage. In addition, the sterilely filtered amniotic fluid may be distributed in vials equipped with special rubber stoppers for sterile lyophilization.

The lyophilization is carried out in a sterile environment. The rubber stoppers on the vials are then automatically pushed down in the freeze dryer to definitively close them. Then an aluminum cap is sealed on each vial to protect its sterile content. In such a lyophilized state, the amniotic fluid may be stored at +4° C. or room temperature for at least one year without decrease of its biological activity. For its medical use, the sterile amniotic fluid may be reconstituted by adding the initial volume of sterile water to the powder in order to restore a transparent and homogeneous physiological liquid.

The decellularization and purification process protects the growth factors and other biological components of amniotic fluid from chemical and enzymatic degradation. Molecules contained within the fluid are stabilized against degradation, avoiding the need for chemical or physical modification to maintain the biological activity of the molecules over extended periods of time. Therefore, D-HAF prepared according to the described methods can be stored for long periods of time, allowing for a broad range of application methods, including distribution and storage as aerosols, solutions, powders, etc.

In some embodiments, the sterile D-HAF is refrigerated at about 1° C. to about 10° C. for long-term storage. In a further embodiment, the sterile D-HAF is refrigerated at 4° C. for up to 12 months and more. For example, fluids purified according to the described methods retain the biological properties of the component molecules over extended periods of storage, ideally without the need for freeze/thawing.

Preferably, the long-term storage does not reduce the quantity of the total soluble proteins or factors present in the D-HAF. For some embodiments, the total soluble proteins retained after long-term storage in refrigerated conditions is about 10%, 20%, 30%, 40%, 50%, 60%, 70%, 80%, or 90% of the fresh D-HAF.

The protein quantities remaining soluble in the D-HAF after a period of storage is assessed by common protein quantification methods such as bicinchoninic acid (BCA) assay, Bradford assay, Lowry assay, and ultraviolet absorption (at 280 nm). To quantify individual proteins, high-throughput methods such as high-density screening arrays (RayBiotech, Norcross Ga.) are used.

Further, the storage does not reduce, prevent or otherwise alter the biological activity of any one or more of the amniotic factors of the DHAF. For example, in some embodiments, the biological activity of one or more amniotic factors is retained throughout storage for extended periods of time. The activity of any one or more of the amniotic growth factors of the stored product can be assessed as a % compared to that of the fresh (raw) product, or compared to the D-HAF prior to storage. Therefore, in some embodiments, little or no statistically significant changes in the biological activity of the amniotic factors are observed when using D-HAF stored at 4° C. for up to a day, 2 days, 3 days, 4 days, 5 days, 6 days, up to one week, up to 2 weeks, up to 3 weeks, up to 4 weeks, up to one month, up to 2 months, up to 3 months, up to 4 months, up to 5 months, up to 6 months or more than 6 months. In other embodiments, the activity of any one of the proteins in the amniotic fluid are reduced by 50%, 40%, 30%, 20%, 10%, 5%, or less than 5% relative to the raw amniotic fluid prior to the de-cellularizing process.

In some embodiments, one or more of the growth factors is reduced after storage. For example, such growth factors include FGF7, MMP-9, GCSF, MMP-7, MMP-13, TGF-β, FGF-4, EG-VEGF and IL-8. In other embodiments, one or more of the growth factors is reduced after freeze/thawing. For example, such growth factors include FGF-21, ANG2, GDNF, FGF-19, TIMP-2, ANG-1, TGFβ1 and M-CSF. In a preferred embodiment, one or more of the growth factors is increase compared to the fresh D-HAF, presumably due to enhanced stability at these storage conditions. Some exemplary growth factors include VEGF-α, TNF-α, and HGF. In a further embodiment, variable changes in the growth factors such as angiotensinogen, PDGF-AA, TGF-α, EGF and SCF.

In some embodiments, inflammatory markers are decreased after refrigeration at 2-8° C. for one, two, three or four weeks. For example, the amount of one or more of the inflammatory proteins present in the refrigerated sample is reduced by about 1%, 5%, 10%, 20%, 30%, 40%, 50%, 60% 70%, or 80% compared to that of the fresh (raw) product. Some exemplary inflammatory markers include Eotaxin-2, IL-6, CCL18, total GRO, CXCL5, 6Ckine, and MIP-3α.

In some embodiments, inflammatory proteins are decreased after freezing. For example, the amount of one or more of the inflammatory proteins present in the sample stored in frozen condition at about −20° C. to about −80° C. is reduced by about 5%, 10%, 20%, 30%, 40%, 50%, 60% 70%, 80% or 90% compared to that of the fresh (raw) product. Some exemplary inflammatory markers include IL-1α, CXCL9, MIP-1α, and CCL5.

In other embodiments, inflammatory markers are increased after being stored for long-term either in refrigerated or frozen conditions. Some exemplary inflammatory markers include TNF-α, MIP-1β, and MCP-2.

In a preferred embodiment, anti-inflammatory molecules are not significantly decreased after being stored refrigerated or frozen for one or more days, weeks or months. In another embodiment, one or more of the anti-inflammatory molecules is decreased in D-HAF following a period of refrigeration. Some exemplary anti-inflammatory molecules include IL-8, IL-13, IL-27, CTLA-4, and IL-21. In another embodiment, one or more of the anti-inflammatory molecules is decreased in the D-HAF stored in frozen conditions. Some exemplary anti-inflammatory molecules include IL-1Ra and TGFβ1.

C. Formulations

The D-HAF is packaged into sterile dosage units which can be stored and distributed for use by attending physicians. These lyophilized or fluid formulations can be in the form of sterile packaged syringes for injection, dropper bottles (typically a 30 day supply for application once or twice daily to the eye), aerosols, or tubes or jars of creams or lotions. The dosages for the Injectables will be 0.25 cc/0.5 cc and 1.0 cc. The injectables can be administered subcutaneously ("sc"), intramuscularly ("im"), or into a joint. The efficacy is determined by Physician evaluations, patient self evaluations, imaging studies and Quality of life evaluations.

The sterile amniotic fluid formulation can be administered in concentrated form, diluted with sterile water or buffer, formulated as a gel, ointment or lotion, solution, suspension or aerosol. It can include additional therapeutic, prophylactic or diagnostic agent, either in the solution, gel, ointment or suspension, or as particles (nanoparticles, liposomes, microparticles) or implants.

Representative excipients include solvents, diluents, pH modifying agents, preservatives, antioxidants, suspending agents, wetting agents, viscosity modifiers, tonicity agents, stabilizing agents, and combinations thereof. Suitable pharmaceutically acceptable excipients are preferably selected from materials which are generally recognized as safe (GRAS), and may be administered to an individual without causing undesirable biological side effects or unwanted interactions. D-HAF can be formulated for storage as a fluid or solid (i.e., powder). In preferred embodiments, DHAF is formulated for storage as a liquid (i.e., above freezing temperatures).

Solutions, Gels, Ointments and Suspensions

Numerous formulations are known and available. Solutions can be the sterile filtered amniotic fluid, concentrated or diluted with water, buffered saline, or an equivalent, formed into a gel with a polysaccharide such as alginate or hyaluronic acid, polyvinyl pyrrole, or ointment such as petrolatum or mineral oil, or emulsified with lipid or oil. Emulsions are generally dispersions of oily droplets in an aqueous phase. There should be no evidence of breaking or coalescence. Suspensions contain solid particles dispersed in a liquid vehicle; they must be homogeneous when shaken gently and remain sufficiently dispersed to enable the correct dose to be removed from the container. A sediment may occur, but this should disperse readily when the container is shaken, and the size of the dispersed particles should be controlled. The active ingredient and any other suspended material must be reduced to a particle size small enough to prevent irritation and damage to the cornea. They may contain suitable additives, such as antimicrobial agents, antioxidants, and stabilizing agents.

When the solution is dispensed in a multidose container that is to be used over a period of time longer than 24 hours, a preservative must be added to ensure microbiologic safety over the period of use.

Formulations should be prepared depending on the intended use of the DC-HAF and are well-known to those skilled in the art. In some embodiments, ophthalmic ointments are sterile, homogeneous, semi-solid preparations intended for application to the conjunctiva or the eyelids. They are usually prepared from non-aqueous bases, e.g. soft paraffin (Vaseline), liquid paraffin, and wool fat. They may contain suitable additives, such as antimicrobial agents, antioxidants, and stabilizing agents.

For example, for ophthalmic application, the pH of the formulations should be ideally equivalent to that of tear fluid, which is 7.4. However, the decision to add a buffering agent should be based on stability considerations. The pH selected should be the optimum for both stability of the active pharmaceutical ingredient and physiological tolerance. If a buffer system is used, it must not cause precipitation or deterioration of the active ingredient. The influence on the lachrymal flow should also be taken into account.

Although solutions with the same pH as lacrimal fluid (7.4) are ideal, the outer surfaces of the eye tolerate a larger range, 3.5 to 8.5. The normal useful range to prevent corneal damage is 6.5 to 8.5. The final pH of the solution is often a compromise, because many ophthalmic drugs have limited solubility and stability at the desired pH of 7.4. Buffers or pH adjusting agents or vehicles can be added to adjust and stabilize the pH at a desired level. Ophthalmic solutions are ordinarily buffered at the pH of maximum stability of the drug(s) they contain. The buffers are included to minimize any change in pH during the storage life of the drug; this can result from absorbed carbon dioxide from the air or from hydroxyl ions from a glass container. Changes in pH can affect the solubility and stability of drugs; consequently, it is important to minimize fluctuations in pH. The buffer system should be designed sufficient to maintain the pH throughout the expected shelf-life of the product, but with a low buffer capacity so that when the ophthalmic solution is instilled into the eye, the buffer system of the tears will rapidly bring the pH of the solution back to that of the tears. Low concentrations of buffer salts are used to prepare buffers of low buffer capacity.

The preparation of aqueous ophthalmic drops requires careful consideration of the need for isotonicity, a certain buffering capacity, the desired pH, the addition of antimicrobial agents and/or antioxidants, the use of viscosity-increasing agents, and the choice of appropriate packaging. Ophthalmic drops are considered isotonic when the tonicity is equal to that of a 0.9% solution of sodium chloride. The eye can usually tolerate solutions equivalent to 0.5-1.8% of sodium chloride.

Solutions that are isotonic with tears are preferred. An amount equivalent to 0.9% NaCl is ideal for comfort and should be used when possible. The eye can tolerate tonicities within the equivalent range of 0.6-2% NaCl without discomfort. There are times when hypertonic ophthalmic solutions are necessary therapeutically, or when the addition of an auxiliary agent required for reasons of stability supersedes the need for isotonicity. A hypotonic ophthalmic solution will require the addition of a substance (tonicity adjusting agent) to attain the proper tonicity range.

The most widely used ophthalmic buffer solutions are boric acid vehicle and Sorensen's modified phosphate buffer. The boric acid vehicle is a 1.9% solution of boric acid in purified water or preferably sterile water. It is isotonic with tears. It has a pH of approximately 5 and is useful when extemporaneously compounding ophthalmic solutions of drugs that are most stable at acid pH. This vehicle does not possess large buffer capacity, but it is sufficient to stabilize pH for the short expiratory periods used for compounded solutions, without overwhelming the natural buffers in lacrimal fluid. The second most commonly used buffer solution is the Sorensen's modified phosphate buffer and is used for drugs needing pH values within the range of 6.5-8.0. This buffer uses two stock solutions, one acidic containing $NaH_2PO_4$, and one basic containing $Na_2HPO_4$. The formulas for the stock solutions and their respective proportions used to obtain specific pH ranges.

In some instances, the formulation is distributed or packaged in a liquid form. Alternatively, formulations for administration can be packed as a solid, obtained, for example by lyophilization of a suitable liquid formulation. The solid can be reconstituted with an appropriate carrier or diluent prior to administration.

Solutions, suspensions, or emulsions for ocular administration may be buffered with an effective amount of buffer necessary to maintain a pH suitable for ocular administration. Suitable buffers are well known by those skilled in the art and some examples of useful buffers are acetate, borate, carbonate, citrate, and phosphate buffers.

Solutions, suspensions, or emulsions for ocular administration may also contain one or more tonicity agents to adjust the isotonic range of the formulation. Suitable tonicity agents are well known in the art and some examples include glycerin, mannitol, sorbitol, sodium chloride, and other electrolytes.

Solutions, suspensions, or emulsions for administration may also contain one or more preservatives to prevent bacterial contamination. Suitable preservatives are known in the art, and include polyhexamethylenebiguanidine (PHMB), benzalkonium chloride (BAK), stabilized oxychloro complexes (otherwise known as PURITE®), phenylmercuric acetate, chlorobutanol, sorbic acid, chlorhexidine, benzyl alcohol, parabens, thimerosal, and mixtures thereof.

Solutions, suspensions, or emulsions for administration may also contain one or more excipients known art, such as dispersing agents, wetting agents, and suspending agents.

In the preferred embodiments, D-HAF formulations do not contain any additives but are packaged in sterile form.

D-HAF formulations containing amniotic factors can be supplied as a clear one-part solution in a suitable container for storage at 4° C., or for storage at −20° C., or at −80° C. For example, liquid formulations in prefilled aliquots can be suitable for storage at 1-5° C., or for storage at −20° C., or at −80° C. The liquid formulation can be suitable for instillation, injection or topical application. In other embodiments, the fluid can be supplied as a kit that can be stored at 4° C., at −20° C., or at −80° C. until needed.

Additional Therapeutic, Prophylactic or Diagnostic Agents

In addition to the one or more therapeutic, prophylactic or diagnostic agents, the formulation can contain one or more additional therapeutic, diagnostic, and/or prophylactic agents. The active agents can be a small molecule active agent or a biomolecule, such as an enzyme or protein, polypeptide, or nucleic acid. Suitable small molecule active agents include organic and organometallic compounds. In some instances, the small molecule active agent has a molecular weight of less than about 2000 g/mol, more preferably less than about 1500 g/mol, most preferably less than about 1200 g/mol. The small molecule active agent can be a hydrophilic, hydrophobic, or amphiphilic compound.

In some cases, one or more additional active agents may be encapsulated in, dispersed in, or otherwise associated with particles in the formulation. In certain embodiments, one or more additional active agents may also be dissolved or suspended in the pharmaceutically acceptable carrier.

In the case of pharmaceutical compositions for the treatment of ocular diseases, the formulation may contain one or more ophthalmic drugs to treat, prevent or diagnose a disease or disorder of the eye. Non-limiting examples of ophthalmic drugs include anti-glaucoma agents, anti-angiogenesis agents, anti-infective agents, anti-inflammatory agents, growth factors, immunosuppressant agents, anti-allergic agents, and combinations thereof.

Representative anti-glaucoma agents include prostaglandin analogs (such as travoprost, bimatoprost, and latanoprost), beta-andrenergic receptor antagonists (such as timolol, betaxolol, levobetaxolol, and carteolol), alpha-2 adrenergic receptor agonists (such as brimonidine and apraclonidine), carbonic anhydrase inhibitors (such as brinzolamide, acetazolamine, and dorzolamide), miotics (i.e., para-sympathomimetics, such as pilocarpine and ecothiopate), seretonergics muscarinics, dopaminergic agonists, and adrenergic agonists (such as apraclonidine and brimonidine).

Representative anti-angiogenesis agents include, but are not limited to, antibodies to vascular endothelial growth factor (VEGF) such as bevacizumab (AVASTIN®) and rhuFAb V2 (ranibizumab, LUCENTIS®), and other anti-VEGF compounds including aflibercept (EYLEA®); MACUGEN® (pegaptanim sodium, anti-VEGF aptamer or EYE001) (Eyetech Pharmaceuticals); pigment epithelium derived factor(s) (PEDF); COX-2 inhibitors such as celecoxib (CELEBREX®) and rofecoxib (VIOXX®); interferon alpha; interleukin-12 (IL-12); thalidomide (THALOMID®) and derivatives thereof such as lenalidomide (REVLIMID®); squalamine; endostatin; angiostatin; ribozyme inhibitors such as ANGIOZYME® (Sirna Therapeutics); multifunctional antiangiogenic agents such as NEOVASTAT® (AE-941) (Aeterna Laboratories, Quebec City, Canada); receptor tyrosine kinase (RTK) inhibitors such as sunitinib (SUTENT®); tyrosine kinase inhibitors such as sorafenib (Nexavar®) and erlotinib (Tarceva®); antibodies to the epidermal grown factor receptor such as panitumumab (VECTIBIX®) and cetuximab (ERBITUX®), as well as other anti-angiogenesis agents known in the art.

Anti-infective agents include antiviral agents, antibacterial agents, antiparasitic agents, and anti-fungal agents. Representative antiviral agents include ganciclovir and acyclovir. Representative antibiotic agents include aminoglycosides such as streptomycin, amikacin, gentamicin, and tobramycin, ansamycins such as geldanamycin and herbimycin, carbacephems, carbapenems, cephalosporins, glycopeptides such as vancomycin, teicoplanin, and telavancin, lincosamides, lipopeptides such as daptomycin, macrolides such as azithromycin, clarithromycin, dirithromycin, and erythromycin, monobactams, nitrofurans, penicillins, polypeptides such as bacitracin, colistin and polymyxin B, quinolones, sulfonamides, and tetracyclines.

In some cases, the active agent is an anti-allergic agent such as olopatadine and epinastine.

Anti-inflammatory agents include both non-steroidal and steroidal anti-inflammatory agents. Suitable steroidal active agents include glucocorticoids, progestins, mineralocorticoids, and corticosteroids.

The ophthalmic drug may be present in its neutral form, or in the form of a pharmaceutically acceptable salt. In some cases, it may be desirable to prepare a formulation containing a salt of an active agent due to one or more of the salt's advantageous physical properties, such as enhanced stability or a desirable solubility or dissolution profile.

Generally, pharmaceutically acceptable salts can be prepared by reaction of the free acid or base forms of an active agent with a stoichiometric amount of the appropriate base or acid in water or in an organic solvent, or in a mixture of the two; generally, non-aqueous media like ether, ethyl acetate, ethanol, isopropanol, or acetonitrile are preferred. Pharmaceutically acceptable salts include salts of an active agent derived from inorganic acids, organic acids, alkali metal salts, and alkaline earth metal salts as well as salts formed by reaction of the drug with a suitable organic ligand (e.g., quaternary ammonium salts). Lists of suitable salts are found, for example, in Remington's Pharmaceutical Sciences, 20th ed., Lippincott Williams & Wilkins, Baltimore, Md., 2000, p. 704. Examples of ophthalmic drugs sometimes administered in the form of a pharmaceutically acceptable salt include timolol maleate, brimonidine tartrate, and sodium diclofenac.

In some cases, the active agent is a diagnostic agent imaging or otherwise assessing the eye. Exemplary diagnostic agents include paramagnetic molecules, fluorescent compounds, magnetic molecules, and radionuclides, x-ray imaging agents, and contrast media.

In certain embodiments, the pharmaceutical composition contains one or more local anesthetics. Representative local anesthetics include tetracaine, lidocaine, amethocaine, proparacaine, lignocaine, and bupivacaine. In some cases, one or more additional agents, such as a hyaluronidase enzyme, is also added to the formulation to accelerate and improves dispersal of the local anesthetic.

Particles and Implants Containing One or More Therapeutic, Prophylactic or Diagnostic Agents Dispersed in a Polymer Matrix Particles can also be formed containing one or more therapeutic, prophylactic or diagnostic agents dispersed or encapsulated in a polymeric matrix. The matrix can be formed of non-biodegradable or biodegradable matrices, although biodegradable matrices are preferred. The polymer is selected based on the time required for in vivo stability, i.e. that time required for distribution to the site where delivery is desired, and the time desired for delivery.

Representative synthetic polymers are: poly(hydroxy acids) such as poly(lactic acid), poly(glycolic acid), and poly(lactic acid-co-glycolic acid), polyanhydrides, polyorthoesters, polyamides, polycarbonates, polyalkylenes such as polyethylene and polypropylene, polyalkylene glycols such as poly(ethylene glycol) (also referred to poly(ethylene oxide)), polyalkylene terephthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, celluloses such as alkyl cellulose, hydroxyalkyl celluloses, cellulose ethers, cellulose esters, nitro celluloses, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt (jointly referred to herein as "synthetic celluloses"), polymers of acrylic acid, methacrylic acid or copolymers or derivatives thereof including esters, poly (methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-co-caprolactone), copolymers and blends thereof. As used herein, "derivatives" include polymers having substitutions, additions of chemical groups, for example, alkyl, alkylene, hydroxylations, oxidations, and other modifications routinely made by those skilled in the art.

Examples of preferred biodegradable polymers include polymers of hydroxy acids such as lactic acid and glycolic acid, and copolymers with PEG, polyanhydrides, poly(ortho)esters, polyurethanes, poly(butyric acid), poly(valeric acid), poly(lactide-co-caprolactone), blends and copolymers thereof.

The in vivo stability of the matrix can be adjusted during the production by using polymers such as polylactide-co-glycolide copolymerized with polyethylene glycol (PEG). PEG if exposed on the external surface may elongate the time these materials circulate since it is hydrophilic.

Particles having an average particle size of between 10 nm and 1000 microns are useful in the compositions described herein. In preferred embodiments, the particles have an average particle size of between 10 nm and 100 microns, more preferably between about 100 nm and about 50 microns, more preferably between about 200 nm and about 50 microns. In certain embodiments, the particles are nanoparticles having a diameter of between 500 and 700 nm. The particles can have any shape but are generally spherical in shape.

Microparticle and nanoparticles can be formed using any suitable method for the formation of polymer micro- or nanoparticles known in the art. The method employed for particle formation will depend on a variety of factors, including the characteristics of the polymers present in the polymer-drug conjugate or polymer matrix, as well as the desired particle size and size distribution. The type of therapeutic, prophylactic or diagnostic agent(s) being incorporated in the particles may also be a factor as some therapeutic, prophylactic or diagnostic agents are unstable in the presence of certain solvents, in certain temperature ranges, and/or in certain pH ranges.

In circumstances where a monodisperse population of particles is desired, the particles may be formed using a method which produces a monodisperse population of nanoparticles. Alternatively, methods producing polydisperse nanoparticle distributions can be used, and the particles can be separated using methods known in the art, such as sieving, following particle formation to provide a population of particles having the desired average particle size and particle size distribution.

Common techniques for preparing microparticles and nanoparticles include, but are not limited to, solvent evaporation, hot melt particle formation, solvent removal, spray drying, phase inversion, coacervation, and low temperature casting. Suitable methods of particle formulation are briefly described below. Pharmaceutically acceptable excipients, including pH modifying agents, disintegrants, preservatives, and antioxidants, can optionally be incorporated into the particles during particle formation.

Implants can be formed from one or more polymers. In preferred embodiments, the implants are intraocular implants. Suitable implants include, but are not limited to, rods, discs, wafers, and the like.

Implants can also be formed from a polymeric matrix having one or more therapeutic, prophylactic or diagnostic agents dispersed or encapsulated therein. The matrix can be formed of any of the non-biodegradable or biodegradable polymers described above, although biodegradable polymers are preferred. The composition of the polymer matrix is selected based on the time required for in vivo stability, i.e. that time required for distribution to the site where delivery is desired, and the time desired for delivery.

The implants may be of any geometry such as fibers, sheets, films, microspheres, spheres, circular discs, rods, or plaques. Implant size is determined by factors such as toleration for the implant, location of the implant, size limitations in view of the proposed method of implant insertion, ease of handling, etc.

Where sheets or films are employed, the sheets or films will be in the range of at least about 0.5 mm×0.5 mm, usually about 3 to 10 mm×5 to 10 mm with a thickness of about 0.1 to 1.0 mm for ease of handling. Where fibers are employed, the fiber diameter will generally be in the range of about 0.05 to 3 mm and the fiber length will generally be in the range of about 0.5 to 10 mm.

The size and shape of the implant can also be used to control the rate of release, period of treatment, and drug concentration at the site of implantation. Larger implants will deliver a proportionately larger dose, but depending on the surface to mass ratio, may have a slower release rate. The particular size and geometry of the implant are chosen to suit the site of implantation.

Intraocular implants may be spherical or non-spherical in shape. For spherical-shaped implants, the implant may have a largest dimension (e.g., diameter) between about 5 µm and about 2 mm, or between about 10 µm and about 1 mm for administration with a needle, greater than 1 mm, or greater than 2 mm, such as 3 mm or up to 10 mm, for administration by surgical implantation. If the implant is non-spherical, the implant may have the largest dimension or smallest dimension be from about 5 µm and about 2 mm, or between about 10 µm and about 1 mm for administration with a needle, greater than 1 mm, or greater than 2 mm, such as 3 mm or up to 10 mm, for administration by surgical implantation.

The vitreous chamber in humans is able to accommodate relatively large implants of varying geometries, having lengths of, for example, 1 to 10 mm. The implant may be a cylindrical pellet (e.g., rod) with dimensions of about 2 mm×0.75 mm diameter. The implant may be a cylindrical pellet with a length of about 7 mm to about 10 mm, and a diameter of about 0.75 mm to about 1.5 mm. In certain embodiments, the implant is in the form of an extruded filament with a diameter of about 0.5 mm, a length of about 6 mm, and a weight of approximately 1 mg. In some embodiments, the dimension are, or are similar to, implants already approved for intraocular injection via needle: diameter of 460 microns and a length of 6 mm and diameter of 370 microns and length of 3.5 mm.

Intraocular implants may also be designed to be least somewhat flexible so as to facilitate both insertion of the implant in the eye, such as in the vitreous, and subsequent accommodation of the implant. The total weight of the implant is usually about 250 to 5000 µg, more preferably about 500-1000 µg. In certain embodiments, the intraocular implant has a mass of about 500 µg, 750 µg, or 1000 µg.

Implants can be manufactured using any suitable technique known in the art. Examples of suitable techniques for the preparation of implants include solvent evaporation methods, phase separation methods, interfacial methods, molding methods, injection molding methods, extrusion methods, coextrusion methods, carver press method, die cutting methods, heat compression, and combinations thereof. Suitable methods for the manufacture of implants can be selected in view of many factors including the properties of the polymer/polymer segments present in the implant, the properties of the one or more therapeutic, prophylactic or diagnostic agents present in the implant, and the desired shape and size of the implant. Suitable methods for the preparation of implants are described, for example, in U.S. Pat. No. 4,997,652 and U.S. Patent Application Publication No. US 2010/0124565.

In certain cases, extrusion methods may be used to avoid the need for solvents during implant manufacture. When using extrusion methods, the polymer/polymer segments and therapeutic, prophylactic or diagnostic agent are chosen so as to be stable at the temperatures required for manufacturing, usually at least about 85 degrees Celsius. However, depending on the nature of the polymeric components and the one or more therapeutic, prophylactic or diagnostic agents, extrusion methods can employ temperatures of about 25° C. to about 150° C., more preferably about 65° C. to about 130° C.

Implants may be coextruded in order to provide a coating covering all or part of the surface of the implant. Such coatings may be erodible or non-erodible, and may be impermeable, semi-permeable, or permeable to the Therapeutic, prophylactic or diagnostic agent, water, or combinations thereof. Such coatings can be used to further control release of the therapeutic, prophylactic or diagnostic agent from the implant.

Compression methods may be used to make the implants. Compression methods frequently yield implants with faster release rates than extrusion methods. Compression methods may employ pressures of about 50-150 psi, more preferably about 70-80 psi, even more preferably about 76 psi, and use temperatures of about 0° C. to about 115° C., more preferably about 25° C.

III. Methods of Administration

A. Disorders and Diseases to be Treated

The D-HAF has a variety of uses based on the concentrations of growth factors and low toxicity and inflammation. The formulation is intended to alleviate pain, inflammation, tissue injury or degeneration. In one embodiment, the formulation is injected into areas with wrinkles, thin skin, or poor healing. In another embodiment, the formulation is administered directly to the eye to treat dry eye due to aging or long term contact use. In another embodiment, the formulation is administered as an aerosol to alleviate one or more symptoms of chronic obstructive pulmonary disease ("COPD"). In another preferred embodiment, the D-HAF is administered into a joint to alleviate pain or enhance healing.

Eye Disorders to be Treated

Examples of eye disorders that may be treated according to the compositions and methods disclosed herein include disorders due to age, damage from traum or infection, autoimmune disease and surgery such as cataract surgery. These include keratitis, conjunctivitis, corneal dystrophic diseases, Fuchs' endothelial dystrophy, dry eye due to Sjogren's syndrome, Stevens-Johnson syndrome, and other autoimmune dry eye diseases, and environmental dry eye diseases, corneal neovascularization diseases, post-corneal transplant rejection prophylaxis and treatment, some types of uveitis, edema, degeneration, and retinopathies. Other disorders which may be treated include injury, burn, or abrasion of the cornea, cataracts and long time contact lens use.

Case studies have shown an immediate positive disease modification for patients with mild to moderate and severe dry eye syndrome, glaucoma, Sjogren's syndrome, possible Ankylosing spondylitis and age-related declining vision. Due to the viscosity of D-HAF, drops applied directly onto the eye adhere to the ocular surface longer than common over the counter ("OTC") artificial tear formulas. The capacity to adhere to the ocular surface is paramount when treating injuries and diseases such as Sjogrens Syndrome and chemical burns. Some unexpected results reported in the study were perceptible improvement to clarity of vision which had been diminished in several patients. Relief from varying levels of ocular discomfort or pain was observed. Nine (9) patients were administered Snell Eye Chart exams at the start and completion of the initial 30 day study of the D-HAF therapy. Five of the nine demonstrated enriched visual acuity and consistently conveyed improvements in visual clarity, distance and reading ability. Improvements of one to several lines on the test charts were recorded. Only two patients tested at undetectable improvement levels. Visual acuity appeared to be correlated to the level of corneal integrity of the recipient. This was another unexpected benefit from the D-HAF therapy and treatments. Other unexpected benefits were being able to read at night for the first time in years and regaining the visual ability required to drive a car. Most participants were able to discontinue or drastically reduce the amount and frequency of using additional applications of artificial tears ("AT") drops and or alternate curatives. One participant diagnosed with mild dry eye exhibited no signs of the disease at the end of the initial 30 day trial.

Joint Disorders to be Treated

Many joint condition may be treated, including pain, arthritis, degeneration, cartilage wear or tear, and damaged joints (such as fracture). The formulation may also be administered to bones that have had prosthetic implants, pins, screws or plates attached or implanted into them, to promote healing and repair, and to reduce inflammation. Injections may be administered to assist in resurfacing and repair or regeneration of cartilage. The formulation may also be administered to assist in soft tissue repair, such as repair of torn or strained ligaments or tendons.

In one embodiment, the formulation is administered at the site of injury. In another embodiment, the formulation is sprayed onto, soaked into, or powder dispersed onto the implant or prosthetic. This can include matrices, implants and sutures.

Treatment of Fibrotic Disease

The formulation can be administered for treatment of some disorders associated with fibrosis or scarring. In one embodiment, the formulation is applied via an aerosol or nebulizer for treatment of chronic obstructive pulmonary disorder.

A clinical trial protocol has been designed to demonstrate clinical efficacy. A dose ranging study includes: administering 0.5, 1.0 or 5 mls/3 mls nebulizing solution.

B. Dosages and Dosing Regimens

Dosage and dosing regimens are dependent on the intended use of the formulation, and is known to those skilled in the art.

In some embodiments, the lyophilized D-HAF is reconstituted by adding the initial volume of water. In other embodiments, the formulation is further diluted to from about 1% to about 99% of the reconstituted D-HAF. The refrigerated formulation is readily diluted to from about 1% to about 99% of the original D-HAF to a desired concentration for applications. In other embodiments, the final formulation is prepared as a much more concentrated solution depending on the need and route of application. In one embodiment, the lyophilized D-HAF is reconstituted by adding half of the initial volume of water to achieve twice as concentration solutions of all amniotic factors. In a further embodiment, the lyophilized D-HAF is reconstituted by adding 10% of the initial volume of water to achieve 10-fold more concentrated solutions of the amniotic factors for application. In some embodiments: the refrigerated D-HAF can be used to reconstitute the lyophilized D-HAF in order to obtain a more concentrated solution.

In the case of sustained or controlled release formulations, ointments, implants or injections into the eye, the dosages will be modified to deliver a therapeutically equivalent amount.

Dosages and Dosing for Treatment of Eye Disorders

In some embodiments, a human amniotic fluid formulation and method of use thereof have been developed for topical application to the eye. The method involves the management of a specifically formulated diluted sterile de-cellularized human amniotic fluid applied directly to the eye(s), preferably as a liquid ocular solution, much like a common liquid eye drops, lubricant or gel. The formulation delivered to the surface of the eye can alleviate or prevent at least one symptom of a number of ocular injuries and diseases, including in addition to chronic dry eye disease, Sjogren's syndrome, and bums or injuries, corneal neovascular disorders, corneal opacities (including corneal haze), prolonged redness and inflammation of the eye(s).

D-HAF has been tested and shown to contain over 300 human growth which can stimulate the proliferation of stem cells, thereby accelerating healing and contributing to modifying the advancement of disease. Due to the viscosity of D-HAF, drops applied directly onto the eye adhere to the ocular surface longer than common OTC artificial tear formulas. The capacity to adhere to the ocular surface is paramount when treating injuries and diseases such as Sjogrens Syndrome and chemical burns.

Unlike Human Amniotic Membrane treatments, in the preferred embodiment, D-HAF is a single daily or twice daily application provided by a licensed ophthalmic profession for in-home use by patients. It should be understood that it may be possible to decrease the dosage and/or the frequency of administration over time as the condition of the eye improves. For example, although initially administered daily, frequency could be reduced to every other day, twice per week, weekly, biweekly or even monthly as a maintenance dose. Therefore, nonsurgical ophthalmologists and Optometrists can dispense and oversee the therapy, giving patients greater choices and access to treatment. In addition, unlike the surgical application of HAM, daily applications of D-HAF deliver a sustainable level of beneficial growth factors. Further, D-HAF requires much less manipulation during processing and is sterilized without the harsh terminal irradiation or e-beam required for HAM.

The concentration and dosage (number of times per day of amount of formulation for period of time) will vary depending on the condition to be treated, the severity of the condition, and the inclusion of other therapeutic, prophylactic or diagnostic agents. The appropriate amounts are determined on an individual basis, measuring response to treatment over time, as demonstrated in the examples.

The dilution ratio of the D-HAF will be dependent on the severity of the disorder or injury; for example, early to moderate dry eye or chronic redness, surface inflammation and, intraocular inflammation may be best treated with a low concentration, whereas, Sjogren's Syndrome, severe Dry Eye, a corneal neovascular disorder, or corneal opacity may dictate a higher concentration of D-HAF.

Dosages and Dosing for Treatment of Joints

Similar considerations apply to treatment of joint injuries, where variables include the size of the joint, the severity of the injury to be treated, the purpose, for example, to enhance healing following surgery may require a shorter term higher dose as compared to more long term, lower dosages for treatment age related damage.

The standard protocol is a series of three injections that can be done daily, every other day, once a week, biweekly, once a month, or at longer intervals, depending on the indication and on the severity of the injury or inflammation. Dosing frequency or dosage may be decreased over time.

In some embodiments, the formulations are prepared for injections into affected areas such as painful joints. In preferred embodiments, the larger hip and shoulder joints get 1.9 cc of PDA Human Amniotic Fluid and the smaller joints get 0.5 cc and the fingers and feet get 0.25 cc.

Since there is no toxicity known to be associated with the formulation, it can be injected as often as the physician chooses, unlike steroids that can only be injected infrequently, typically two to three times a year.

The present invention will be further understood by reference to the following non-limiting examples.

EXAMPLES

Example 1: Preparation of Human Amniotic Formulation

Materials and Methods

Human amniotic fluid is collected from selected caesarean sections, which make aspiration of the amniotic fluid in clean condition possible. Then the amniotic fluid is stored in refrigerated condition at 2° C. to 6° C. before the clarification and filtration process. The amniotic fluid is centrifuged at 5,000 to 10,000 rpm for 30 minutes to 1 hour in 50 mL to 250 mL swing out buckets. The supernatant is collected. When collecting the supernatant it is important to avoid detaching or aspirating insoluble components possibly coming from the pellet or from the fatty overlayer. If the supernatant still contains residual insoluble components, it may be pre-filtered with 5 to 10μ cellulose ester capsule pre-filters without TRITON® surfactant to avoid contamination in the filtration process. The liquid phase is collected and filtered with poly ether sulfone 1.0μ capsule filters and the liquid is collected. The liquid is then filtered with poly ether sulfone 0.2μ capsule filter. The filtrate is transferred to vials and sealed with stoppers aseptically. Four samples from the final filtrate are taken to test whether the sterile filtered human amniotic fluid retains growth factors, such as human growth hormone, transforming growth factor beta 1, vascular endothelial growth factor, epidermal growth factor, transforming growth factor beta 3.

Results

The results show retention of growth factors. The concentration of the growth factors in the sterile filtered amniotic fluid is from about 30 pg/mL to about 2500 pg/mL. Except the vascular endothelial growth factor in sample 2, the concentrations of all the factors in the four samples are in the range of 30-150 pg/mL. Although part of growth differentiation factor 11 is lost in centrifugation and filtration, the final sterile filtered amniotic fluid still retains about 17% to 29% of growth differentiation factor from the raw human amniotic fluid.

Example 2: Long-Term Storage of Sterile Filtered Amniotic Fluid

Materials and Methods

Preparation of Aliquots for Storage

The sterile D-HAF prepared according to Example 1 was either frozen at −85° C. or was refrigerated at 2-8° C. for two weeks prior to the protein array analysis. Raw amniotic fluid directly harvested from a woman without any centrifugation or filtration steps was used as a control.

Protein Array Analysis

To quantify individual proteins, high-density screening arrays (RayBiotech, Norcross Ga.) were used.

Results

D-HAF as a raw fluid i.e. freshly collected and sterile filtered amniotic fluid was analyzed against D-HAF that was stored either at −85° C. or at 2-8° C. The total amount of protein remained in the −85° C. sample and 2-8° C. sample was about 82.3% and 89.8% of the raw fluid, respectively (FIG. 1).

Figure 2:
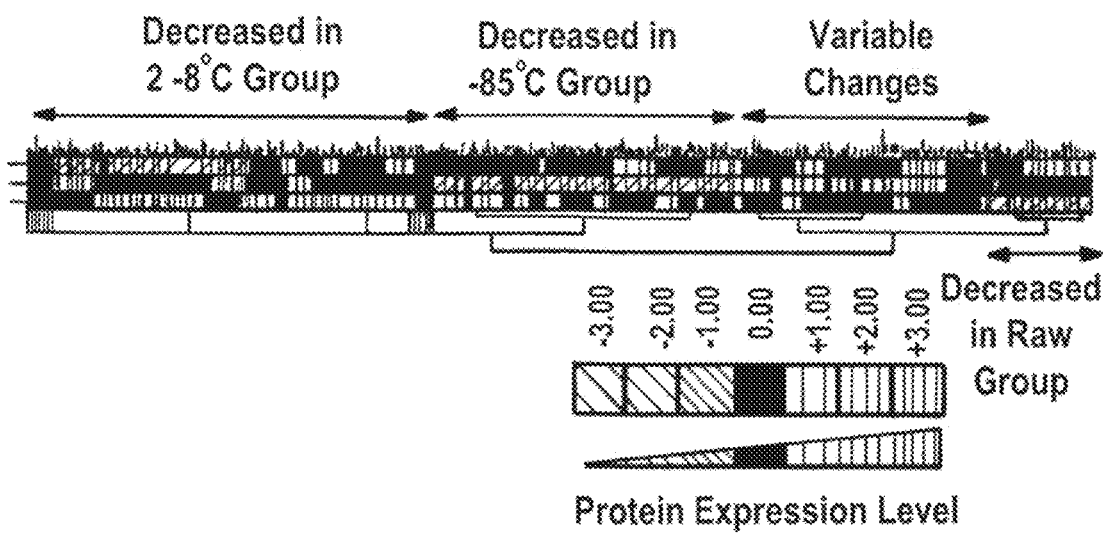
FIG. 2 is a global heat map showing relative amount of individual proteins in the raw fluid, the −85° C. sample and the 2-8° C. sample of the D-HAF.
Figure 3A:
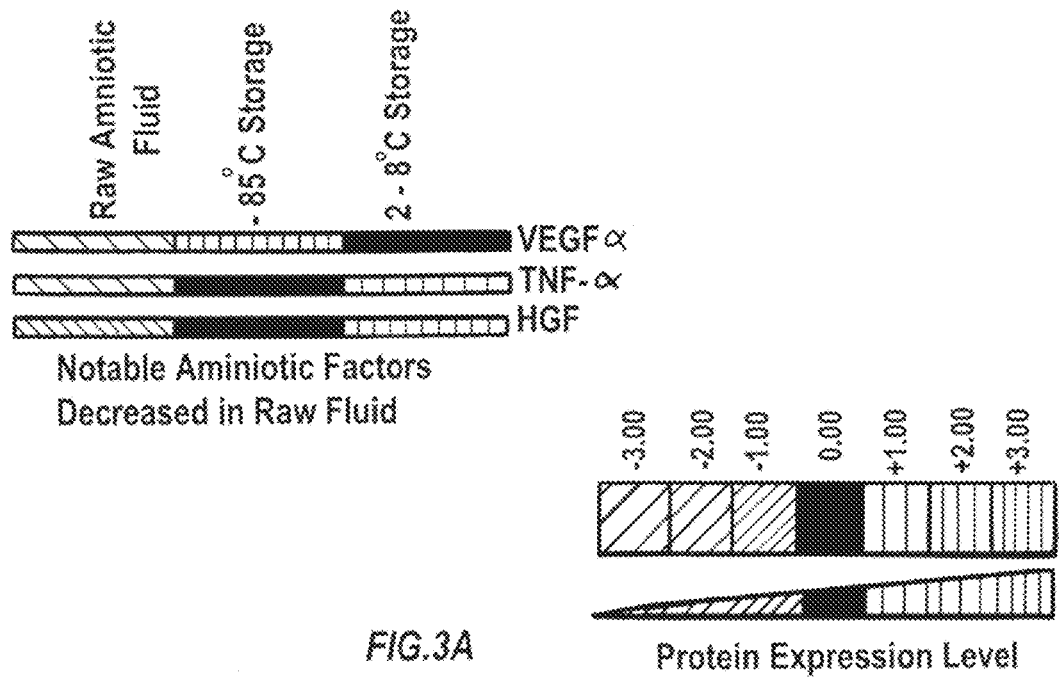
FIGS. 3A-3D are heat maps showing relative amount of individual amniotic factors in the raw fluid, the −85° C. sample and the 2-8° C. sample of the D-HAF.
Figure 3B:
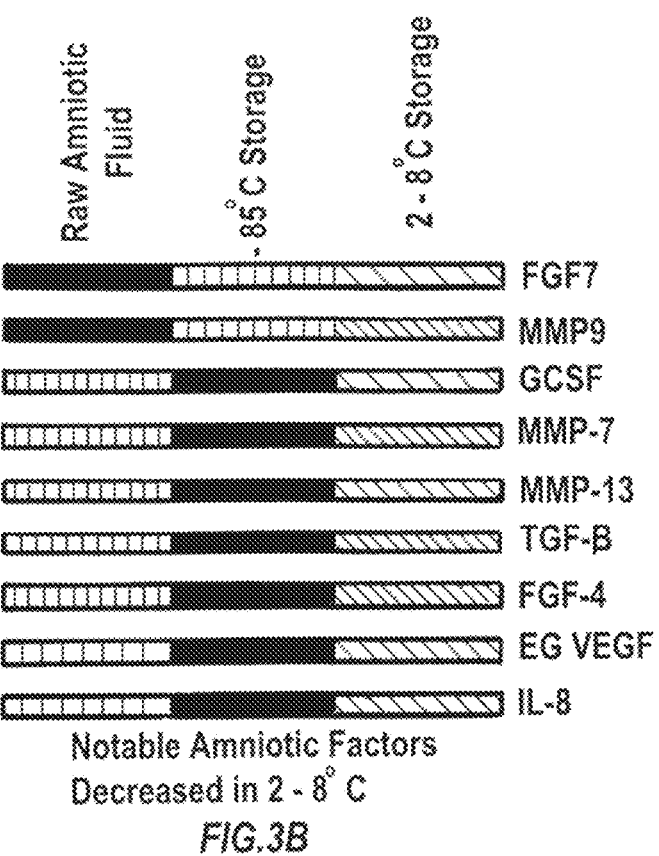
Figure 3C:
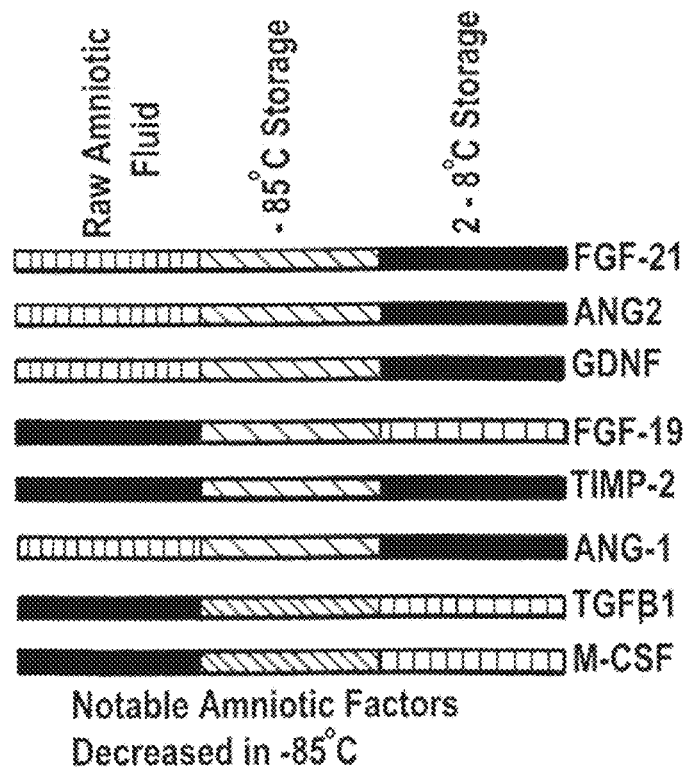
Figure 3D:
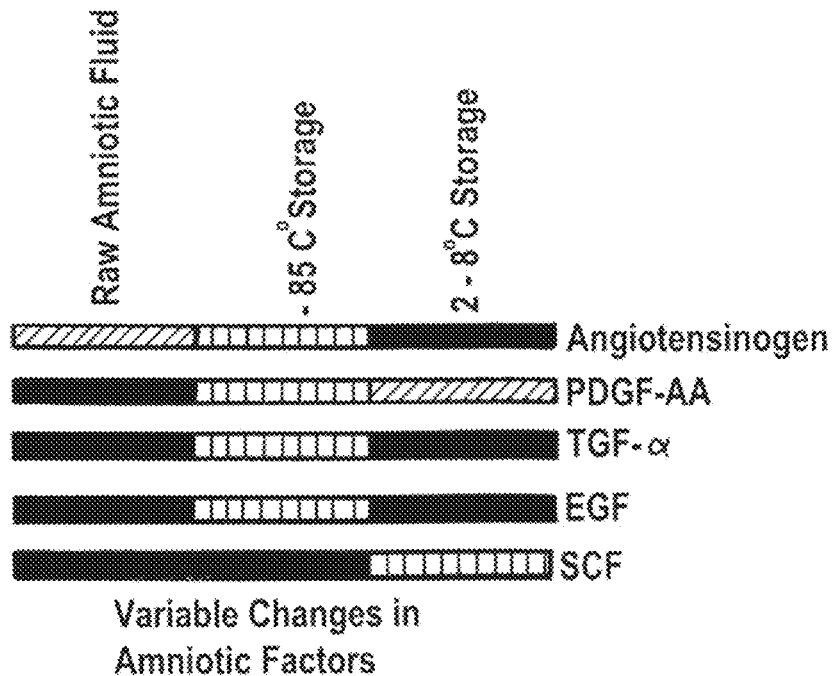
Figure 4A:
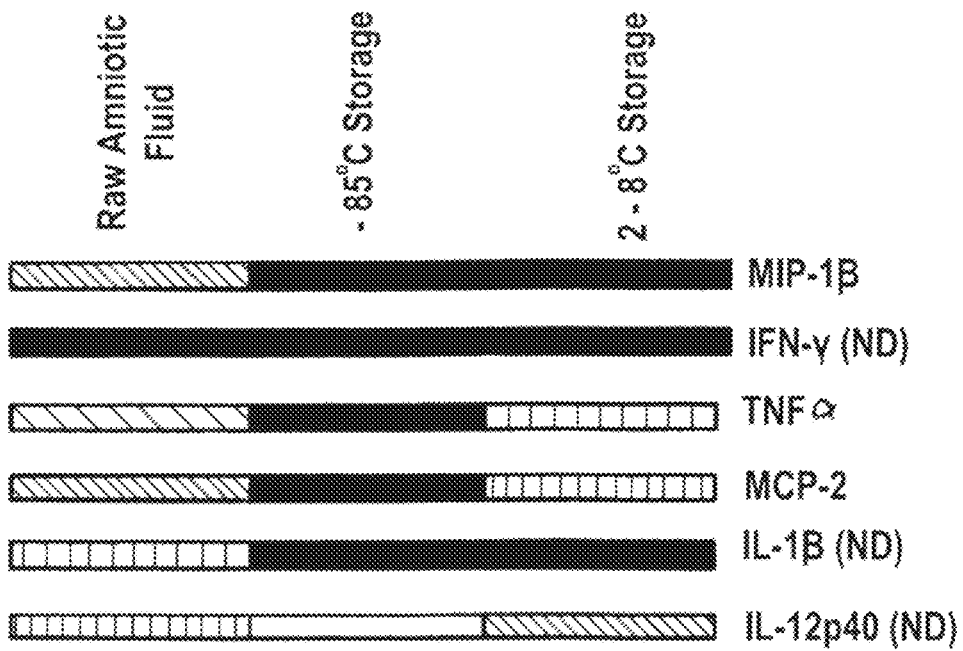
FIGS. 4A-4C are heat maps showing relative amount of individual inflammatory factors in the raw fluid, the −85° C. sample and the 2-8° C. sample of the D-HAF.
Figure 4B:
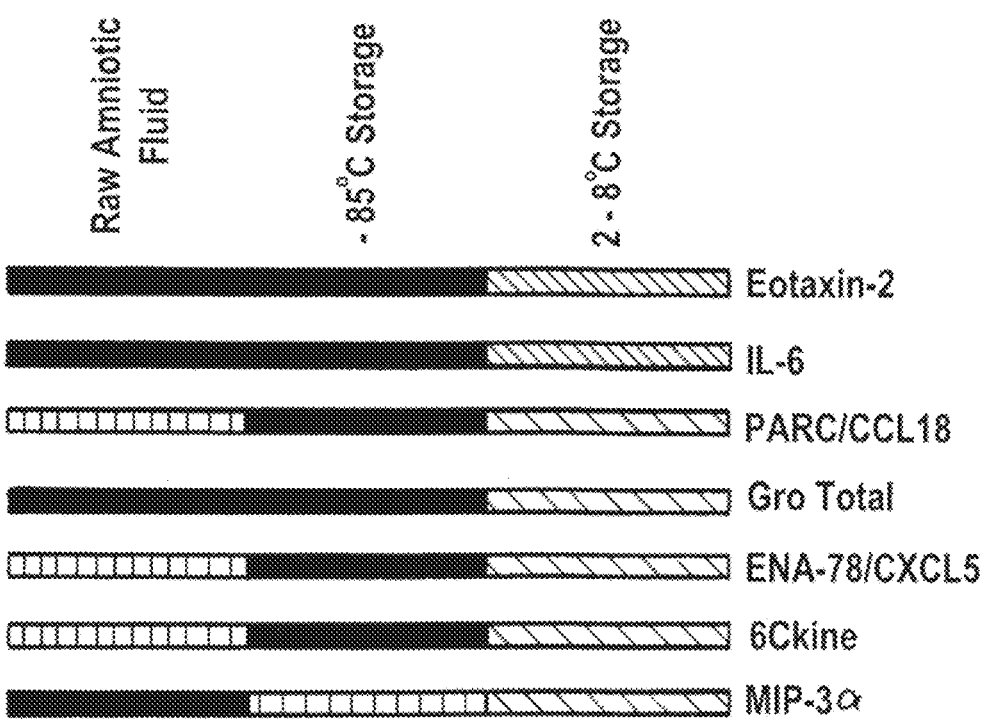
Figure 4C:
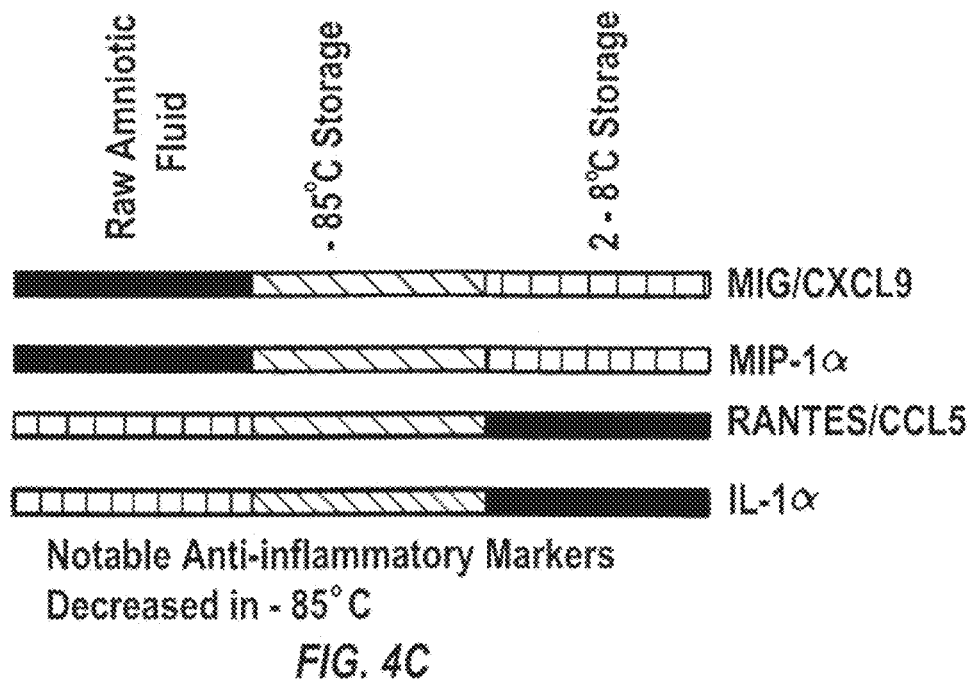
Figure 5A:
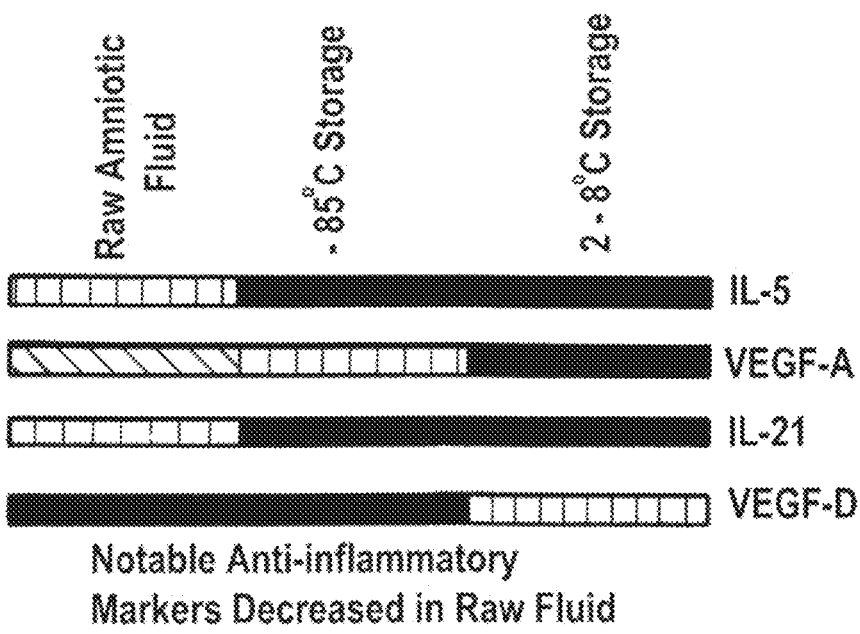
FIG. 5A-5C are heat maps showing relative amount of individual anti-inflammatory factors in the raw fluid, the −85° C. sample and the 2-8° C. sample of the D-HAF.
Figure 5B:
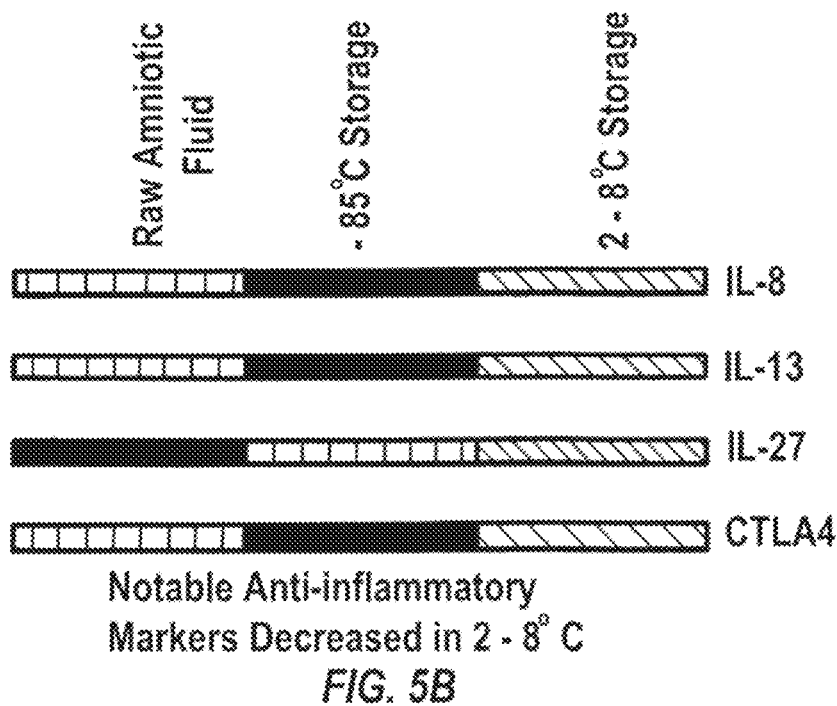
Figure 5C:
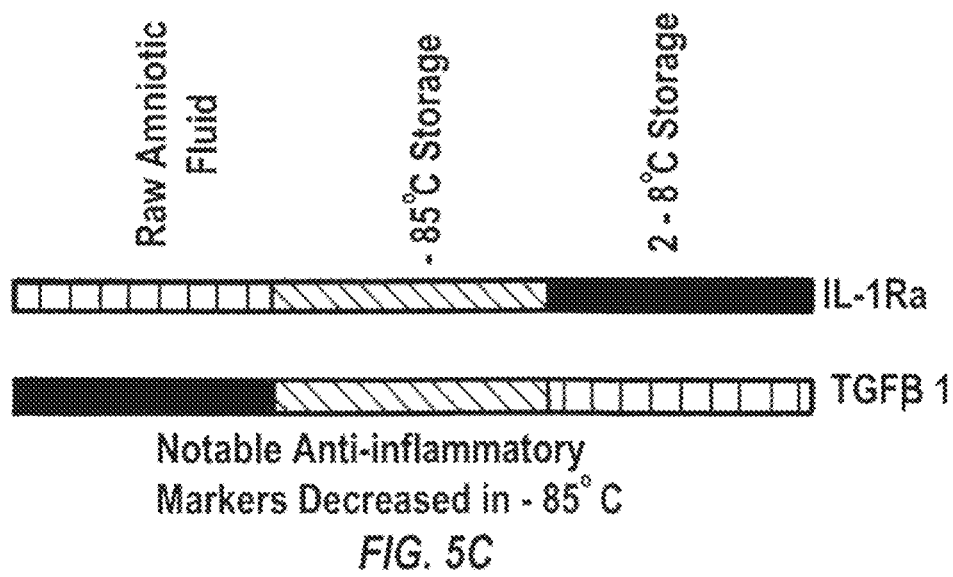

When compared using protein arrays, the raw fluid was the least changed and most concentrated for the majority of the protein targets (FIG. 2). The hierarchical clustering analysis revealed that the sample stored at 2-8° C. was most closely related to the raw fluid. Refrigeration (i.e. stored at 2-8° C.) kept the majority of the proteins at the same or higher levels than the raw fluid. The sample stored at −85° C. was the most different among the three groups, although still over 50% of the targets remained at similar or higher levels than the raw fluid samples.

Specifically, several classes of protein targets were examined to assess the feasibility of various storing methods. These proteins include amniotic factors, inflammatory proteins and anti-inflammatory proteins.

Amongst notable amniotic growth factors that were altered in the three groups, VEGF-α, TNF-α and HGF were relatively decreased in the raw fluid. Several amniotic growth factors that were relatively decreased in the refrigerated sample include FGF7, MMP-9, GCSF, MMP-7, MMP-13, TGF-β, FGF-4, EG-VEGF and IL-8. Notable amniotic growth factors decreased in the −85° C. sample include FGF-21, ANG2, GDNF, FGF-19, TIMP-2, ANG-1, TGFβ1 and M-CSF. Other variable changes noted amongst the three groups were angiotensinogen, PDGF-AA, TGF-α, EGF and SCF.

The most dramatic decrease observed in the 2-8° C. group was with many inflammatory factors and such targets include Eotaxin-2, IL-6, PARC/CCL18, total GRO, ENA-78/CXCL-5, 6Ckine and MIP-3α being significantly decreased after being refrigerated. Fewer inflammatory factors were decreased in the −85° C. sample, including MIG/CXCL-9, MIP-1α, RANTES/CCL-5 and IL-1α. Notable inflammatory factors decreased in the raw fluid include MIP-1β, TGFα and MCP-2. Some inflammatory factors that were not detected in any of these samples include IFN-β, IL-1β and IL-12p40.

Changes in common anti-inflammatory markers were spread fairly equally across all groups. IL-8 and IL-13 were decreased in the 2-8° C. sample, while they were slightly elevated in the raw fluid. CTLA-4 was significantly reduced in the refrigerated sample. IL-27 and CTLA-4 were both reduced in the refrigerated sample compared to the other two groups. VEGF-D was elevated in the refrigerated sample. IL-1Ra and TGFβ1 were reduced in the −85° C. group. IL-5, IL-21, and VEGF-D were all reduced in the raw fluid. IL-10, IL-13, VEGFα were below the limit of detection.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

I claim:

1. A composition consisting of sterile, de-cellularized human amniotic fluid (D-HAF) comprising a combination of growth factors, pro-inflammatory factors, and anti-inflammatory factors derived from raw amniotic fluid in an effective amount to reduce inflammation, promote wound healing, assist tissue repair, or a combination thereof,
wherein the D-HAF is not concentrated, diluted, or heat-treated relative to the raw fluid.

2. The composition of claim 1, wherein the D-HAF is prepared by a process comprising de-cellularizing the raw amniotic fluid to remove cells or particulate matter.

3. The composition of claim 2, wherein the process further comprises incubating the de-cellularized amniotic fluid at a temperature between about 1° C. and about 20° C. for a period of time effective to reduce the quantity of one or more inflammatory factors relative to the raw amniotic fluid.

4. The composition of claim 3, wherein the temperature is between about 2° C. and about 8° C.

5. The composition of claim 3, wherein the period of time for incubating the de-cellularized amniotic fluid is about one or more days, weeks, months, or up to a year.

6. The composition of claim 5, wherein the period of time for incubating the de-cellularized amniotic fluid is between about one day and about two weeks.

7. The composition of claim 3, wherein one or more of the pro-inflammatory factors are reduced by about 1%, 5%, 10%, 20%, 30%, 40%, 50%, 60% 70%, or 80% compared to the one or more of the pro-inflammatory factors in the raw amniotic fluid.

8. The composition of claim 7, wherein one or more of the pro-inflammatory factors are reduced by at least 10% compared to the one or more of the pro-inflammatory factors in the raw amniotic fluid.

9. The composition of claim 1, wherein the growth factors are selected from the group consisting of epidermal growth factor (EGF), insulin-like growth factor I (IGF-I), vascular endothelial growth factor A (VEGF-α), tumor necrosis factor A (TNF-α), hepatocyte growth factor (HGF), fibroblast growth factor 7 (FGF7), matrix metallopeptidase (MMP-9), granulocyte-colony stimulating factor (GCSF), matrix metalloproteinase-7 (MMP-7), matrix metalloproteinase-7 (MMP-13), transforming growth factor alpha (TGF-α), transforming growth factor beta (TGF-β), fibroblast growth factor 4 (FGF-4), endocrine gland-derived vascular endothelial growth factor (EG-VEGF), interleukin 8 (IL-8), fibroblast growth factor 21 (FGF-21), angiopoietin-2 (ANG2), Glial cell-derived neurotrophic factor (GDNF), fibroblast growth factor 19 (FGF-19), TIMP metallopeptidase inhibitor 2 (TIMP-2), angiopoietin-1 (ANG-1), transforming growth factor beta 1 (TGFβ1), macrophage colony-stimulating factor (M-CSF), angiotensinogen, platelet derived growth factor-AA (PDGF-AA), stem cell factor (SCF), and a combination thereof.

10. The composition of claim 1, wherein the pro-inflammatory factors are selected from the group consisting of Eotaxin-2 (CCL24), interleukin 6 (IL-6), pulmonary and activation-regulated chemokine PARC or chemokine (C-C motif) ligand 18 (CCL18), total GRO which consisted of three subunits GROα/CXCL1, GROβ/CXCL2, and GROγ/CXCL3, expression of the neutrophil-activating CXC chemokine (ENA-78/CXCL-5), chemokine (C-C motif) ligand 21 (CCL21 or 6Ckine), macrophage inflammatory protein 3 alpha (MIP-3α or CCL20), monokine induced by gamma (MIG or CXCL-9), MIP-1α, chemokine (C-C motif) ligand 5 (CCL-5), Interleukin-1 alpha (IL-1α), macrophage inflammatory protein-1β (MIP-1β or CCL4), tumor necrosis factor (TNFα), monocyte chemotactic protein 2 (MCP-2 or CCL8), and a combination thereof.

11. The composition of claim 1, wherein the anti-inflammatory factors are selected from the group consisting of interleukin 8 (IL-8), interleukin 13 (IL-13), interleukin 27 (IL-27), cytotoxic T-lymphocyte-associated protein 4 (CTLA-4), vascular endothelial growth factor D (VEGF-D), interleukin-1 receptor antagonist (IL-1Ra), transforming growth factor beta 1 (TGFβ1), interleukin 5 (IL-5), interleukin 21 (IL-21), and a combination thereof.

12. The composition of claim 1, wherein the D-HAF retains about 10%, 20%, 30%, 40%, 50%, 60%, 70%, 80%, or 90% of total amniotic proteins compared to the raw amniotic fluid.

13. The composition of claim 12, wherein the D-HAF retains at least 50% of the amniotic proteins compared to the raw amniotic fluid.

14. A pharmaceutical composition consisting of sterile, de-cellularized human amniotic fluid (D-HAF) prepared by a process comprising de-cellularizing raw amniotic fluid to remove cells or particulate matter, wherein the D-HAF comprises a combination of growth factors, pro-inflammatory factors, and anti-inflammatory factors in an amount effective to reduce inflammation, promote wound healing, assist tissue repair, or a combination thereof, and
pharmaceutically acceptable excipients.

15. A medical implant comprising sterile, de-cellularized human amniotic fluid (D-HAF) of claim 1.

16. A kit comprising the sterile, de-cellularized human amniotic fluid (D-HAF) of claim 1.

17. A method for reducing inflammation, promoting wound healing, or assisting tissue repair comprising administration to a subject in need thereof the composition of claim 1.

18. The method of claim 17, wherein the subject has a disorder selected from the group consisting of eye disorders, joint disorders, and pulmonary disorders.

* * * * *